United States Patent [19]

Nowinski et al.

[11] Patent Number: 4,843,010

[45] Date of Patent: * Jun. 27, 1989

[54] POLYMERIZATION-INDUCED SEPARATION IMMUNOASSAYS

[75] Inventors: Robert C. Nowinski; Allan S. Hoffman, both of Seattle, Wash.

[73] Assignee: Genetic Systems Corporation, Seattle, Wash.

[*] Notice: The portion of the term of this patent subsequent to Apr. 16, 2002 has been disclaimed.

[21] Appl. No.: 574,558

[22] Filed: Jan. 27, 1984

Related U.S. Application Data

[63] Continuation-in-part of Ser. No. 550,929, Nov. 10, 1983, Pat. No. 4,511,478.

[51] Int. Cl.⁴ ............................................. G01N 33/537
[52] U.S. Cl. ............................................. 435/7; 435/6; 436/501; 436/504; 436/548; 436/539; 436/548; 525/904; 526/238.1; 527/202
[58] Field of Search ............... 435/6, 7; 436/501, 504, 436/538, 539, 548; 526/238.1; 525/904; 527/202

[56] References Cited

U.S. PATENT DOCUMENTS

| | | | |
|---|---|---|---|
| 3,969,287 | 7/1976 | Jaworek | 526/238.1 |
| 4,469,796 | 9/1984 | Axén | 435/7 |
| 4,474,892 | 10/1984 | Murad | 436/513 |
| 4,609,707 | 9/1986 | Nowinski | 436/531 |

*Primary Examiner*—Robert J. Warden
*Assistant Examiner*—Robert Benson
*Attorney, Agent, or Firm*—Richard L. Neeley

[57] ABSTRACT

Immunoassay methods and compositions are disclosed for the detection of analytes in fluid samples. The disclosure provides conjugates of analytes or reactants with polymerizable organic monomers. Specific binding reactions between reactants are detected by means of resporter/reactant conjugates. Free and specifically-bound reporter/reactant conjugates are separated by a polymerization reaction which renders the polymerized monomers insolule.

20 Claims, 5 Drawing Sheets

POLYMERIZATION-INDUCED SEPARATION IMMUNOASSAYS

CROSS-REFERENCE TO RELATED APPLICATIONS

This application is a continuation-in-part of U.S. patent application Ser. No. 550,929, filed on Nov. 10, 1983, now U.S. Pat. No. 4,511,478.

TECHNICAL FIELD

The present invention relates generally to immunoassay methods and more particularly to an immunoassay in which a polymerization reaction is used to effect a separation of the specific reactants.

BACKGROUND ART

1. Immunoassays

Immunoassays have found widespread application in the field of clinical diagnostics for the detection and measurement of drugs, vitamins, hormones, proteins, metabolites, microogranisms, and other substances of interest (analytes) in biological and non-biological fluids. Typically, these analytes occur in micromolar ($10^{-6}$ M) or less concentration.

Immunoassays generally incorporate antibodies and antigens as reactants, at least one of which is labeled with a signal producing compound (e.g. radioisotope, fluorophore, etc.). Following mixture with the sample and incubation, specific antibody/antigen reactions occur (specific binding). The reaction mixture is subsequently interrogated to detect free and specifically-bound labeled reactant, enabling a measurement of the analyte in the sample.

Immunoassays can be divided into two general categories, homogeneous and heterogeneous. In a homogeneous immunoassay, the signal emitted by the specifically-bound labeled reactant is different from the signal emitted by the free labeled reactant. Hence, bound and free can be distinguished without physical separation.

The archetypal homogeneous immunoassay is the enzyme-multiplied immunoassay technique (EMIT), which is disclosed in U.S. Pat. No. 3,817,837. In this technology, analyte present in patient sample and analyte/enzyme conjugate compete for a limited amount of anti-analyte antibody. Specific binding of antibody to the conjugate modulates its enzymatic activity. Hence, the amount of enzyme activity is proportional to the amount of analyte in the sample. Homogeneous immunoassays have the advantage of being rapid, easy to perform, and readily amenable to automation. Their principal disadvantages are that they are relatively prone to interferences, are generally limited to low molecular weight analytes and are generally limited in sensitivity to approximately $10^{-9}$ M.

In a heterogeneous immunoassay, the signal emitted by the bound labeled reactant is indistinguishable from the signal emitted by the free labeled reactant. Therefore, a separation step is required to distinguish between the two.

Typical heterogeneous immunoassays include the radioimmunoassay (RIA) and the enzyme-linked immunosorbent assay (ELISA). In the RIA, radiolabeled analyte and analyte present in patient sample compete for a limited amount of immobilized (solid phase) anti-analyte antibody. The solid phase is washed to remove unbound labeled analyte and either the bound or the free fraction is analyzed for the presence of labeled reactant. ELISA assays are performed analogously. In this case, though, the signal is an enzyme instead of a radioisotope. Heterogeneous immunoassays typically employ at least one reagent immobilized on a solid phase. Since the kinetics of reaction between an immobilized antibody (or antigen) and its binding site tend to be slower than the kinetics of the same reaction occurring in solution, long incubation times are frequently required. When the multiple wash steps often needed are considered, it can be appreciated that heterogeneous assays tend to be time-consuming and labor-intensive. However, they are in general more sensitive than homogeneous assays and less prone to interferences, since interfering substances can be removed in the wash steps.

Solids used to immobilize reactants in immunoassays have included controlled pore glass and preformed polymers such as polyvinyls, polyacrylamides, polydextrans and polystyrene.

Numerous separation methods are known in the art and have been used in heterogeneous immunoassays. These include centrifugation, filtration, affinity chromatography, gel permeation chromatography, etc.

The homogeneous immunoassay methods of the prior art are generally prone to interferences, of limited sensitivity and have a limited range of antigen sizes. The heterogeneous immunoassays of the prior art, while increasing the sensitivity and minimizing interferences, tend to be time consuming and labor intensive. These difficulties generally arise from the added step of physical separation and the need for numerous washes to decrease background interference.

There is a need in the art for an immunoassay method which is sensitive to sub-micromolar concentrations of analyte; which has fast reaction kinetics; and which minimizes the number of manipulations necessary to achieve a result.

2. Polymer Chemistry

A reaction fundamental to polymer chemistry is the initiation of end-to-end covalent linkages between soluble organic monomers leading to the formation of larger polymeric molecular structures (polymers). Synthetic polymers can be formed from a single monomeric species (homopolymer) or from a mixture of different monomers (co-polymer). Linear, branched, or cross-linked structures are possible. By varying the chemical composition or ratios of the monomers, it is possible to form either soluble or insoluble polymers which comprise a broad range of chemical and physical structures. For example, water-soluble monomers (such as acrylamide) can be copolymerized to form water-soluble homopolymers. They can also be copolymerized with less water-soluble monomers (such as N-alkyl or N, N-dialkyl acrylamides) or with cross-linking monomers (such as N, N'-methylenebisacrylamide) to form water-insoluble copolymer structures. Some water-soluble monomers (such as hydroxyethyl methacrylate or acrylonitrile) can be homopolymerized to form water-insoluble homopolymers.

In the fields of biochemistry and immunology, water-insoluble polymers (such as polysaccharides or polyacrylics, sometimes cross-linked) have been commonly used as solid phase supports with passively absorbed, physically entrapped, or covalently-linked proteins in affinity chromatography, enzyme immobilization, and immunoassay. See, for example, U.S. Pat. Nos. 3,957,741; 4,257,884; 4,195,129; 4,225,784; 4,181,636; 4,401,765; and 4,166,105.

To date, the documented coupling of a polypeptide to a polymer has occurred under circumstances in which the polypeptide was provided in soluble form and the polymer was provided as a preformed soluble or preformed insoluble material. While these polymers are of utility in providing a surface upon which selective biochemical or immunological reactions can occur, the polymers are of limited value in that the spacing, steric accessibility, and number of polypeptides bound per unit length of polymer cannot be precisely or reproducibly controlled. Lot-to-lot variation is commonly encountered during the manufacture of such solid phase polymer/reactant matrices. In certain end-use applications where reproducibility and standardization are essential (e.g. immunoassays), this variation in composition of the solid-phase polymer/reactant matrices presents a critical problem. Consequently, there is a need in the art for a method to specifically tailor or molecularly engineer polymer compounds incorporating controlled quantities of reactants.

DISCLOSURE OF THE INVENTION

The present invention provides immunoassay methods for determining the presence of an analyte in a fluid sample suspected of containing said analyte comprising contacting said fluid sample with a monomer/reactant conjugate in order to form a monomer/reactant conjugate-analyte complex and providing a reporter for said monomer/reactant conjugate--analyte complex, separating said reporter-labeled complex by initiating polymerization of the monomer/reactant conjugate--analyte complex and detecting the incorporation of reporter into said polymerized complex.

Another aspect of the invention provides immunoassay methods utilizing monomer/analyte conjugates for competitive immunoassays.

A further aspect of the invention provides monomer/reactant and monomer/analyte conjugates for use in the immunoassays of the present invention.

A novel feature of this immunoassay is the use of reactant (antibody or antigen) that is covalently linked with a polymerizable organic monomer. Following mixture and reaction of the immunoassay components, the monomer/reactant conjugate and its specific binding complement (i.e., its appropriate antigen or antibody counterpart bound through specific antibody/antigen interactions) can be rapidly and conveniently separated from solution by initiating a polymerization reaction. In contrast to the monomer/reactant conjugate and its specifically bound complement, other components of the immunoassay remain in free solution. Thus, this method provides an effective single-step separation of specifically bound and free reactants.

The polymerization-induced separation immunoassays of the instant invention are believed to offer several advantages over prior art homogeneous and heterogeneous immunoassay methods. Because of the separation achieved by polymerization of the monomer/reactant conjugate, the immunoassay of this invention can achieve the sensitivity typical of state-of-the-art heterogeneous techniques combined with the ease of performance of homogeneous techniques.

The immunoassays of this invention can typically be performed in less time than traditional heterogeneous assays because binding reactions which would normally occur on a solid phase can be made to occur in solution instead. Also, the need for extensive washing of the solid phase can be eliminated.

Sandwich immunoassays typically require elution of the specifically bound labeled reactant from the solid phase prior to measurement. This adds an extra step and makes even longer and more cumbersome an already long and tedious process. The immunoassay of this invention can be performed without the elution of the bound labeled reactant from the polymer, thus simplifying performance.

BEST MODE FOR PRACTICING THE INVENTION

Figure 1:
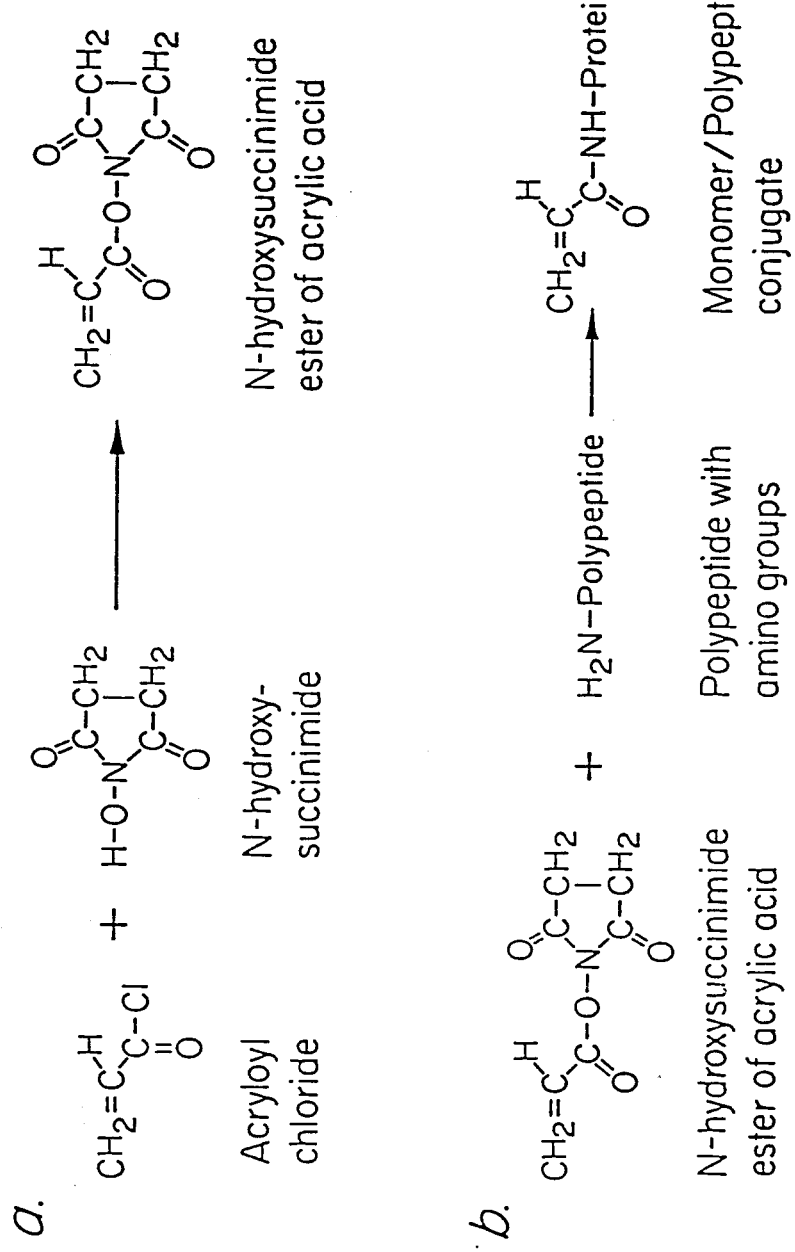
FIG. 1 is a diagrammatic representation of the synthesis of an activated acrylic acid monomer and a conjugation involving this monomer and, for example, amino groups on a reactant of the present invention.

Co-pending United States patent application Ser. No. 550,929 filed on Nov. 10, 1983, which is herein incorporated by reference, discloses methods and compounds for the de novo synthesis of organic polymers that contain polypeptides as an integral part of their backbone structure. This allows one to molecularly engineer polymer compounds incorporating controlled quantities of polypeptides for specific applications. The present invention is directed towards an application of the technology to immunoassays, in which the polypeptides are antigen and antibody reactants.

The methods of this invention for the immunoassay of analytes in biological fluids utilize conjugates of reactants with monomers or signal-producing compounds (monomer/reactant or reporter/reactant conjugates). Separation of free from specifically bound reporter/reactant is effected by a polymerization reaction.

Although the following discussion pertains primarily to the immunoassay of analytes in biological fluids, it will be appreciated that there are numerous disciplines which require the assay of fluid samples for the presence or amount of organic substances. These disciplines include for example food preparation and environmental quality control.

For the purposes of this disclosure, the following terms are defined: Analyte is the substance or group of substances the presence or amount of which it is desired to determine. Biological fluids are blood, blood serum, blood plasma, urine, feces, cerebrospinal fluid, saliva, sputum, cell and tissue derived extracts, etc. in which the analyte is suspected of being contained. Reactants are naturally occurring or synthetic substances, typically antigens and antibodies, which are capable of recognizing and specifically binding to each other. The term antigen as used herein includes molecules which themselves may induce antibodies as well as small molecules which are not capable of eliciting antibody production unless they are coupled to a carrier (e.g. haptens). Epitope is any antigenic determinant. Monomer is any soluble organic compound which is capable of forming end-to-end covalent linkages (i.e. polymerizing) under the appropriate conditions. Reporter is any substance which is capable of producing a detectable signal either alone or in combination with other reagents, such as, e.g., radioisotopes, fluorophores, chromophores, luminescent compounds, etc.

The immunoassays of the present invention can be performed in any of several configurations. These can include competitive, sandwich and non-competitive immunoassay configurations. In every case the analyte of interest can be either an antigen or an antibody. In every case, either reactant (i.e. antigen or antibody) can be conjugated to either labeled substance (i.e. monomer or reporter). The various possible configurations in which immunoassays can be performed are reviewed extensively in *Enzyme-Immunoassay*, E. T. Maggio (Ed.) CRC Press, Boca Raton, Fla. (1980) and numerous other publications.

In one configuration, for example, sample suspected of containing analyte is incubated with a monomer/analyte conjugate and a reporter/reactant conjugate. In this case, the reactant is typically an antibody to the analyte. If the analyte is itself an antibody, the reactant can be a second antibody to the first antibody or it can be the antigen to the first antibody. Analyte present in sample and monomer/analyte conjugate compete for a limited amount of reporter/reactant. Polymerization-induced separation of free from specifically-bound reporter/reactant enables the detection and measurement of analyte initially present in the sample. This configuration is referred to as competitive.

In the competitive configuration, the immunoassays of this invention can be used to measure both monoepitopic compounds (haptens) and multiepitopic compounds. Multiepitopic is meant to include both compounds having more than one unique epitope and compounds having a single, repeated epitope. Maximum sensitivity is generally attained when the reactant is monovalent with respect to the analyte.

In another configuration, the immunoassays of this invention can be performed as sandwich immunoassays. This configuration is appropriate only for multiepitopic analytes. In the forward sandwich configuration, excess monomer/reactant conjugate is incubated with sample suspected of containing analyte. In this case, the reactant is typically an antibody to the analyte. If the analyte is itself an antibody, the reactant in the reporter/reactant conjugate can be either a second antibody to the first antibody or an antigen to the first antibody. Incubation is carried out under conditions in which specific binding is expected to occur. Following polymerization of monomer/reactant, excess reporter/reactant conjugate is added to the immunoassay mixture. Typically, the reactant is an antibody which binds to a different epitope from that to which the monomer/reactant conjugate binds. Again, if the analyte is itself an antibody, the reactant in the reporter/reactant conjugate can be either an antibody to the first antibody or an antigen to the first antibody. After an appropriate incubation to allow specific binding to occur, the presence or amount of reporter/reactant specifically bound to the polymer is determined. The polymer particles can be washed if desired to remove any free reporter/reactant. In general, however, it is thought sufficient to simply dilute the reaction mixture 2 to 100-fold prior to measuring the amount of reporter associated with the polymer particle. Similarly, if desired, the polymer particles can be separated from solution and the reporter associated with them eluted prior to detection or measurement.

The order of addition of reagents can also be reversed, i.e., sample suspected of containing analyte can be incubated with reporter/reactant prior to addition of monomer/reactant conjugate. This configuration is referred to as a reverse sandwich immunoassay. Likewise, sample, reporter/reactant, and monomer/reactant conjugate can be incubated simultaneously rather than sequentially, in which case the immunoassay is referred to as a simultaneous sandwich immunoassay. Of the three possible sandwich configurations, the simultaneous sandwich immunoassay is most preferred because it requires the least number of manipulations. All three configurations, however, offer significant advantages over prior art sandwich immunoassays in that incubation times are shortened and washing steps are eliminated.

In another configuration, the immunoassays of this invention can be performed by incubating patient sample suspected of containing analyte with monomer/reactant conjugate (the reactant being an antibody to the analyte) under conditions where specific binding is expected to occur. Reporter/reactant can be added sequentially or simultaneously but in this case the reactant is an antibody to the monomer/reactant-analyte complex rather than to the analyte. Following polymerization-induced separation of free from specifically-bound reporter/reactant, the presence or amount of reporter/reactant specifically bound to the polymer particles is determined. In this configuration, the first reactant (anti-analyte) can be conjugated to either monomer or reporter. Likewise, the second reactant (anti-first reactant--analyte complex) can be conjugated to either monomer or reporter, whichever was not conjugated to the first reactant. This configuration, which is referred to as non-competitive, offers the advantage that both reactants can be employed in excess. Thus, the sensitivity of the immunoassay is not strictly limited by the affinity constants of the reactants. This configuration is also appropriate for both monoepitopic and multiepitopic analytes.

The immunoassays of this invention utilize a monomer/reactant conjugate. Typically, the reactant is an antibody or an antigen. However, other reactants are known in the art, including e.g. lectins, receptors, transport proteins, and Stapylococcal protein A. Where the reactant is an antibody, either monoclonal or polyclonal antibodies can be used. Prior to conjugation, the antibody will in general be at least partially purified by methods known in the art.

The monomer is typically an ethylenically or acetylenically unsaturated compound containing at least one functionality for coupling to the reactant. Functionalities in the reactant can include, for example, covalently bondable functionalities such as hydroxyl, amine, carboxyl, or sulfhydryl. Olefinically unsaturated monomers can be selected from compounds having the general formula:

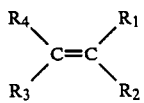

where $R_1$ is H or a lower alkyl radical having from one to eight carbon atoms and $R_2$ can be:

—H

—COCl

—COOH

—CO$_2$(CH$_2$)$_n$OH (n = 1-8)

—CH$_2$NH$_2$

—CH$_2$Cl

—CO$_2$C$_2$H$_4$NHR (R = H or any organic group)

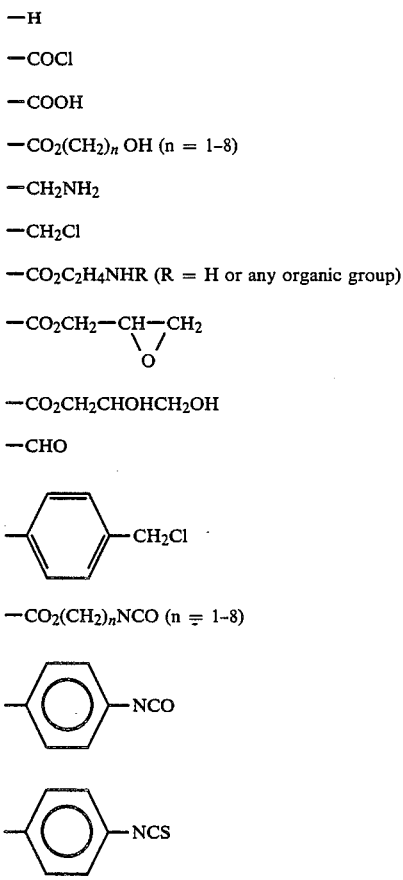

—CO$_2$CH$_2$CHOHCH$_2$OH

—CHO

—CO$_2$(CH$_2$)$_n$NCO (n = 1-8)

$R_3$ and $R_4$ are most usually H, however they can be chosen to provide an unsaturated group, e.g. any allyl monomer:

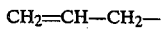

CH$_2$=CH—CH$_2$— a vinylene monomer:

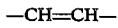

—CH=CH— or a diene monomer:

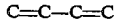

C=C—C=C

Alternatively, $R_2$ and $R_3$ can be combined as, e.g.

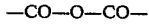

—CO—O—CO— to form

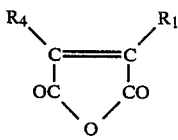

Also, acetylenically unsaturated monomers having a reactable group are also useful:

—C≡C—

In addition, polyunsaturated molecules, oligomers or polymers (generally with defined unsaturation) having reactable groups will be useful. For representative examples see: Hoffman, A. S., "Electron Curing of Coatings," Isotopes and Radiation Technology, 9:1, pp. 78–92 (1971).

Specific monomers which can be used include acrylic acid, methacrylic acid, acryloyl chloride, methacryloyl chloride, glycidyl acrylate or methacrylate, glycerol acrylate or methacrylate, allylamine, allyl chloride, hydroxy-lower alkyl-acrylates (e.g., 2-hydroxyethyl methacrylate (HEMA) or 3-hydroxypropyl methacrylate), and amino lower alkyl-acrylates (e.g., 2-aminoethyl methacrylate).

Preferred monomers are those which are soluble in water or water/polar organic solvent mixtures.

Covalent coupling of the monomer to the reactant or its attached carbohydrate (in the case of glycoprotein reactants) can be carried out by any number of known chemical methods. For example, the monomer and/or the reactant can be activated to produce a stable but chemically reactive intermediate which can be subsequently reacted. The reactant can also be activated by periodate oxidation of the attached carbohydrates, if the reactant is a glycoprotein. This reaction forms aldehydes which can then condense with amino groups on the monomers, such as 2-aminoethyl methacrylate, to form a Schiff base. This Schiff base can be reduced with sodium cyanoborohydride to form a stable covalent linkage. The monomer in the form of an acid halide may also be directly reacted with the reactant in the presence of an acid scavenger to remove acid as it is formed during the reaction. Additionally, bifunctional or hetero-bifunctional reagents may be used. Such bifunctional or hetero-bifunctional reagents are known and can be obtained, for example, from Pierce Chemical Company, Rockford, Ill. In almost all cases, the reaction conditions, i.e., time, temperature, solvent and pH, should be such as to avoid denaturation and/or degradation of the reactant.

Generally a single species of monomer will be conjugated to a selected reactant or analyte. However, it will be appreciated that a mixture of copolymerizable monomers can be conjugated to the reactant or analyte and which are thereafter separated by polymerization.

Homopolymerization of the monomer/reactant conjugate with itself or copolymerization with nonderivatized monomers is initiated by generation of free radicals. Nonderivatized monomers which may be used include, for example, ethylenically and/or acetylenically unsaturated monomers, as previously discussed, alkyl acrylates or methacrylates where the alkyl radical contains from 1 to 8 carbons, acrylonitrile and vinyl acetate. Also, cross-linking compounds may be copolymerized with the monomer/reactant conjugate. Such cross-linking compounds may include, for example, N,N'-methylenebisacrylamide or a di-, tri-or tetramethacrylate or acrylate. The percentage of derivatized and nonderivatized monomer may vary from traces up to 100%, but the preferable range is between 0.001 to 100% derivatized monomer and 0 to 99.999% nonderivatized monomer.

In addition to a monomer/reactant conjugate, a reporter/reactant conjugate is also required. The reporter can be chosen from any of those known in the art, including enzymes, fluorophores, radioisotopes, chemiluminescent materials, dye particles, etc. In general, however, fluorophores are preferred. Some suitable fluorophores include fluorescein, rhodamine, phycoerythrin, and Nile blue.

Generally a single species of reporter will be utilized in the present invention. However, it will be appreciated that a mixture of reporter/reactant conjugates can be provided wherein each selected reactant species is conjugated to a distinct reporter. By utilizing an analogous mixture of monomer/reactant conjugates wherein each selected monomer species has a different reactivity, a sample can be assayed for a plurality of analytes simultaneously.

Methods of coupling the reporter to the reactant or analyte are well-known in the art. In general, covalent coupling is preferred, although other means of attachment are possible. The reactive sites which can be utilized for attachment are the same as those discussed above. In general, it is desirable to label the reactant with reporter as heavily as possible without loss of binding activity.

Separation of the specifically bound from the free reactants is accomplished by polymerization of the monomer/reactant conjugate. Polymerization or copolymerization with nonderivatized monomer is generally conducted at about room temperature with or without agitation. A surface active agent (e.g. detergent) may or may not be present. Although the reaction may be carried out in the presence of oxygen, it is generally preferred to conduct the reaction in the absence of oxygen or in the presence of a controlled amount of oxygen. The pH range may vary widely from pH 3 to pH 10, although it is preferable to select a pH where the reactant remains the most stable, which is typically between pH 6 and 8. If a surface active agent is used, suitable compounds, such as sodium dodecyl sulfate, sodium stearate, or nonionic materials, such as polyethyleneoxide lauryl ether, may be employed.

The free radicals may be generated by oxidation-reduction initiation, photochemical initiation, ionizing radiation or thermal initiation. An advantage of both oxidation-reduction initiation and photochemical initiation is production of free radicals at reasonable rates at relatively low temperatures, such as ambient or body temperature (22°-37° C.). Types of oxidation-reduction initiators which may be used include (1) peroxides in combination with a reducing agent, e.g., hydrogen peroxide with ferrous ion, or benzoyl peroxide with N,N-dialkylaniline or toluidine, and (2) persulfates in combination with a reducing agent, such as sodium metabisulfite or sodium thiosulfate. Specifically, ammonium persulfate, benzoyl peroxide, lauryl peroxide, t-butyl hydroperoxide, t-butyl perbenzoate, cumene hydroperoxide, or mixtures thereof with reducing agents, such as sodium bisulfite or sodium thiosulfate, may be used. It also appears that sodium bisulfite alone may be used for polymerization.

Photoinitiated polymerization may also be used by employing photoinitiators, such as azodiisobutyronitrile, azodiisobutyroamide, benzoin methyl ether, riboflavin, thiazine dyes such as methylene blue and eosin, and transition metals such as ferric chloride or diazidotetramminecobalt (III) azide, in combination with ultraviolet and/or visible light irradiation of the reaction system.

Ionizing radiation may also be employed utilizing radiation from a radioactive source or a particle accelerator.

Polymerization can be carried out in the presence of various physiological materials commonly encountered in biological fluids.

Nonderivatized monomers and polymerization initiating compounds can be present in the reaction mixture throughout the immunoassay or they can be added at any appropriate time. Measurement of the amount of reporter specifically bound to the polymer can be made in any of several ways depending upon the type of signal provided by the reporter. In one preferred embodiment, the reporter is a fluorophore and fluorescence associated with polymer particles is detected or measured by flow cytometry.

The following examples are provided by way of illustration, rather than implying any limitation of the present invention.

EXPERIMENTAL

Examples presented here utilize a representative monomer (2-hydroxyethyl methacrylate, HEMA), two antibodies and an antigen (human IgM) to be detected. The first antibody is a mouse monoclonal designated 2H1, which reacts with the kappa light chain of human IgM and is conjugated with monomer. The second antibody is a mouse monoclonal designated 2C3, which reacts with the mu heavy chain of human IgM and does not interfere with the binding of the first antibody to human IgM. The second antibody is labeled with a fluorescent tag. Briefly stated, these examples utilize a simultaneous sandwich immunoassay configuration in which the presence of the analyte to be detected mediates the incorporation of reporter/reactant (fluorescein labeled 2C3 antibody) into the polymer formed. The amount of reporter/reactant specifically bound to the polymer, i.e. the fluorescence intensity, is proportional to the amount of analyte in the sample. In a typical protocol, the two reactant conjugates are incubated together with the sample suspected of containing analyte to form a ternary complex. Nonderivatized (free) monomer is then added, and subsequent initiation of polymerization results in a copolymerization of nonderivatized monomer with monomer/reactant conjugate present in the ternary complex to form a fluorescent polymer. In the absence of analyte, the reporter/reactant conjugate does not form a ternary complex and the polymer particles are not substantially fluorescent.

Example 1 demonstrates (a) the activation of an acrylic monomer to allow its conjugation to the first reactant, (b) the conjugation of the acrylic monomer to the first reactant including evidence that the conjugation was successful, (c) the demonstration that the monomer/reactant conjugate retained the ability to bind to analyte, and (d) the conjugation of the second reactant with the reporter, fluorescein isothiocyanate. Example II demonstrates the polymerization of HEMA monomer in a buffered saline solution. In order to assure noninterference in this polymerization process by compounds commonly found in or added to biological samples, this reaction was also conducted in the presence of a sample of serum and in the presence of a nonionic detergent. Example III demonstrates an analyte-mediated incorporation of fluorescence into the insoluble polymer particles. This was accomplished by first incubating samples of the monomer/reactant conjugate and the reporter/reactant conjugate either with analyte or with a control buffer solution. After subsequent polymerization the particles formed were analyzed by flow cytometry and the analyte positive sample was found to contain highly fluorescent particles, while the particles contained in the control solution exhibited only background fluorescence. Likewise the extent of this fluorescence incorporation into the particles was found to be directly related to the amount of analyte present, forming the basis for a quantitative immunoassay system.

Example I

A Synthesis of an Activated Acrylic Acid Monomer for Conjugation to Reactant A mixture containing N-hydroxysuccinimide (NHS) (4.6 g, 40 mmol) and acryloyl chloride (18 mL, 220 mmol) was refluxed with vigorous stirring for 3 hours in an anhydrous atmosphere and the reaction mixture, a homogeneous solution, was evaporated to a syrup. Distilled water (50 mL) was added to the syrup and the mixture was stirred for 30 minutes at 4° C. Upon addition of chloroform (50 mL), the mixture was separated into layers, and the organic layer was extracted successively with water (generally 5 times with 50 mL each time) until the pH of the water layer was approximately 5. The aqueous solutions so obtained were combined and extracted once with chloroform (50 mL); this chloroform solution and the chloroform solution from above were combined, dried over sodium sulfate, and evaporated to a syrup. Crystals, obtained by storing the syrup overnight at −20° C., were triturated with diethyl ether, and harvested by filtration.

Recrystallization from absolute ethanol yielded 2.0 g of the desired product. This compound was analyzed by mass spectrometry, infrared spectroscopy, NMR, liquid chromatography, and melting point, and proved to be the N-hydroxysuccinimide ester of acrylic acid (FIG. 1a).

B: Preparation of a Monomer/Reactant Conjugate

The N-hydroxysuccinimide ester of acrylic acid (NSA) was reacted with mouse monoclonal antibody (MAb) 2H1 as follows: 2.2 mg MAb in 0.29 M sodium carbonate buffer, pH 9.3, was added to 20 micrograms of NSA in a total volume of 0.5 mL. The reaction mixture was incubated at 37° C. for one hour with constant stirring. Of this solution, 100 microliters was then taken for an analysis by reversed-phase high-performance liquid chromatography (RP-HPLC), which revealed the amount of free acrylic acid (arising from nonspecific hydrolysis of NSA) and remaining NSA in the reaction mix (Table 1) (FIG. 1b).

TABLE 1

RESULTS OF HPLC ANALYSIS OF MONOMER CONJUGATION REACTION MIXTURE

|  | Antibody | NSA (Activated monomer) | Monomer Acrylic Acid |
|---|---|---|---|
| Amount added, nanomoles | 14.5 | 116.0 | 0.0 |
| Amount detected in solution, nanomoles | not determined | 0.0 | 26.7 |

This indicated that a net of 89 nanomoles of monomer was attached to the 14.5 nanomoles of MAb for a ratio of 6.2 monomer molecules per MAb.

To remove residual NSA and its hydrolysis products and for further characterization of the derivatized antibody, 200 microliters of the reaction mixture was chromatographed on a column of Sephadex ® G-25 (beads of dextran cross-linked with epichlorohydrin from Pharmacia Fine Chemicals AB, Uppsala, Sweden) in the same carbonate buffer to which bovine serum albumin, 0.1 mg/mL, was added to prevent nonspecific adsorption of polypeptides to the Sephadex ® G-25.

A sample of the monomer/reactant conjugate was then analyzed by isoelectric focusing. In this procedure, the polypeptide subunits of the proteins were separated according to their isoelectric point, or pH at which they had no net positive or negative charge. For this purpose, the heavy and light chains of the monomer/reactant conjugate were first dissociated in the presence of 3% (w/v) sodium dodecyl sulfate (SDS) and 5% (v/v) 2-mercaptoethanol and separated on the basis of molecular weight by electrophoresis in an SDS-polyacrylamide slab gel. The separated heavy and light chains of the reactant were cut out from the gel and analyzed further by isoelectric focusing in a polyacrylamide slab gel according to their isoelectric point. Staining of the isoelectric focusing gel with dye (Coomassie Brilliant Blue R-250) provided a characteristic pattern of bands for each sample. Since both the heavy and light chains of antibodies are glycoproteins which contain intrinsic variations in their sialic acid content, each heavy and light chain can be separated by charge into a characteristic family of bands, with each band containing a polypeptide and differing amounts of sialic acid. As the reaction of the activated acrylic acid occurred primarily with amino functional groups on protein lysine residues, the addition of monomer to MAb would be expected to neutralize one positive charge on the protein subunit for each molecule of acrylic acid attached. This in turn would be expected to change the isoelectric point of the derivatized protein.

Figure 2:
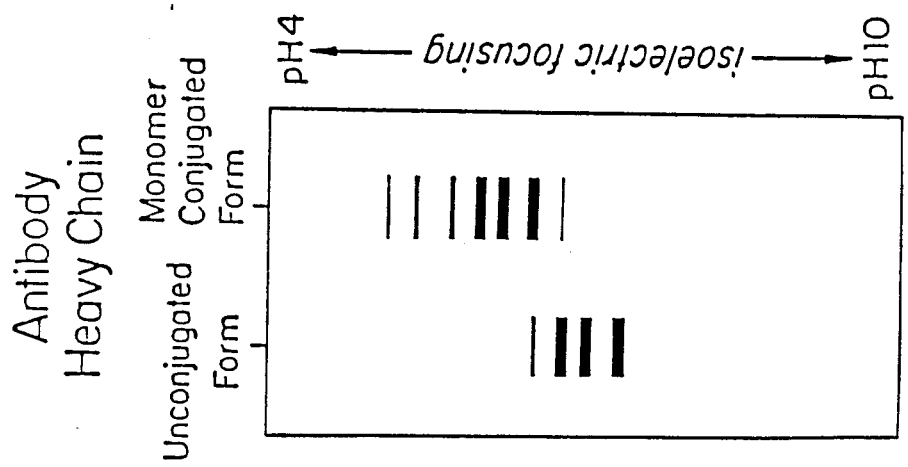
FIG. 2 is a diagrammatic representation of a polyacrylamide isoelectric focusing gel of the heavy chain of antibody reactant 2H1 before and after conjugation with acrylic acid.

The results of the isoelectric focusing analysis indicated that each heavy chain was modified by the covalent attachment of approximately three acrylic monomers (FIG. 2). Analysis also indicated that the electrophoretic pattern of monomer-derivatized light chain was so close to the nonderivatized polypeptide pattern that essentially minimal conjugation of monomer to light chains had occurred. On this basis, it was estimated that six moles of acrylic acid monomer was conjugated to each mole of antibody (3 per heavy chain times 2 heavy chains per antibody), which was in agreement with the analysis by RP-HPLC.

C: Demonstration that the Monomer/Reactant Conjugate Retained Binding Capacity for Analyte To show that the purified monomer/reactant conjugate was still active, it was tested in an enzyme linked immunosorbent assay (ELISA), and the results indicated no loss of specific binding capacity. For this purpose, human IgG (which contain the same kappa chain antigen as human IgM) was adsorbed to the surfaces of wells in a micro ELISA plate (96 wells). The wells were washed, residual nonspecific adsorbing sites on the plastic surface were blocked with bovine serum albumin, and then incubated with serial dilutions of the antibodies (control antibody and monomer/antibody conjugate). The plate was again washed, incubated with goat anti-mouse immunoglobulin conjugated to horseradish peroxidase (Tago, Inc., Burlingame, Calif. 94010), washed, and incubated with the substrates for horseradish peroxidase, o-phenylenediamine and hydrogen peroxide. Dilute aqueous sulfuric acid was added to stop the reaction, the plates were assayed on a micro ELISA reader, and the optical densities of each dilution of monomer/antibody conjugate compared with that of the control antibody. On a molar basis, the monomer/reactant conjugate demonstrated comparable specific binding activity to the nonconjugated antibody alone.

D: Preparation of a Reporter/Reactant Conjugate

The final step in the assembly of the components of a simultaneous sandwich immunoassay system was the identification of a second antibody (2C3, which reacts with the mu heavy chain of human IgM) that bound to a different epitope of the analyte, thus it did not block the binding of the first, monomer/reactant conjugate to the analyte. The second antibody reactant was labeled with a reporter (fluorescein). For this purpose, 60 micrograms (20 microliters of a 3.0 mg/mL solution in DMSO) of fluorescein isothiocyanate isomer II (FITC) was added to 1 milligram of antibody 2C3 in 0.125 mL of 0.27M carbonate buffer, ph 9.3. The mixture was incubated for 30 minutes at 37° C. and chromatographed on a column of Sephadex ® G-25 in phosphate buffered saline to which 0.5M NaCl and 0.1% $NaN_3$ had been added. This separated the fluorescein labeled antibody from any free FITC that remained in solution. The peak was collected in a volume of 0.25 ml and the fluorescein-to-antibody ratio, calculated from the absorbances at 280 nm and 495 nm using the equation F/Ab ratio = $3.1 \times A495/A280 - 0.31 \times A495$, was found to be 4.7. Using methods similar to those in Example I.C, this reporter/reactant was found to be fully capable of specifically binding to analyte.

EXAMPLE II

Polymerization of Hema Monomer in a Buffered Saline Solution

Figure 3:
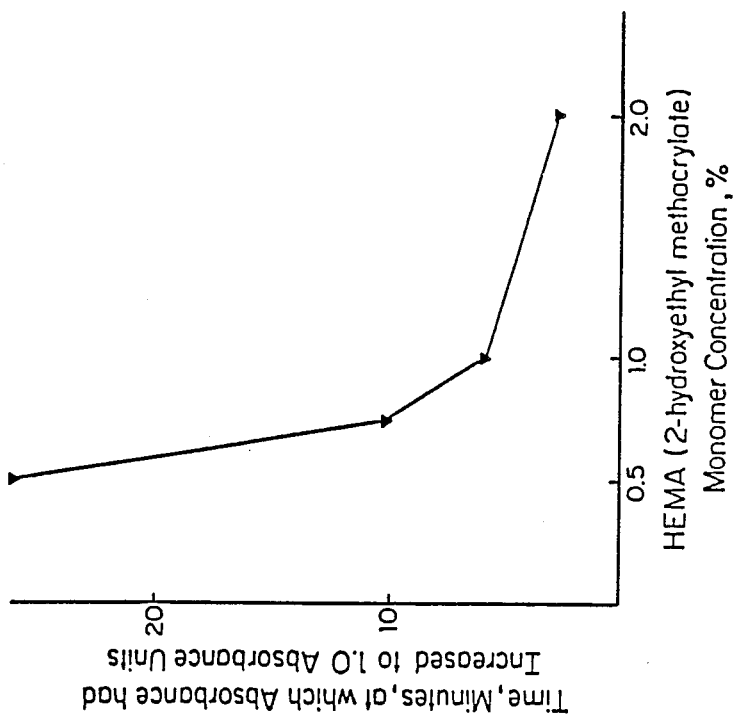
FIG. 3 depicts the effect of monomer 2-hydroxyethyl methacrylate (HEMA) concentration on the rate of formation of insoluble HEMA homopolymer particles.

Polymerization of 2-hydroxyethyl methacrylate in the presence of physiological compounds was carried out as follows: to 2.73 mL of distilled water or phosphate-buffered saline, pH 7.4, was added 0.06 to 0.24 mL of 25% (v/v) 2-hydroxyethyl methacrylate (HEMA, Aldrich Chemical Company). Water was added to a final volume of 2.97 mL, as necessary. After bubbling prepurified nitrogen through a Pasteur pipette into the bottom of the cuvet for at least five minutes, 30 microliters of 1M $Na_2S_2O_5$ was added and the precipitation of the resulting polymer was followed at 550 nm with a Beckman Model 26 spectrophotometer. FIG. 3 illustrates the dependence of the rate of precipitation on the concentration of monomer. From this data, a concentration of 2% was chosen.

Inclusion of fetal calf serum, up to 10% (v/v), or "Nonidet P-40", a nonionic detergent, available from Shell Chemical Co., at concentrations up to 1% (w/v), had no effect on the rate of formation of the polymer particles. Since fetal calf serum contains a variety of proteins and other physiological compounds, this indicates that most proteins and physiological compounds will not inhibit formation of the polymer particles. Since nonionic detergents are commonly used in immunoassays to solubilize biological substances, this indicates that it will be possible to utilize detergents in polymerization-induced separation immunoassays without interference.

EXAMPLE III

Demonstration of Analyte-Specific Incorporation of Fluorescence into Polymer

This example illustrates a simultaneous two antibody sandwich immunoassay method. In this method, the reporter/reactant (fluorescein-labeled 2C3, 5 micrograms), the analyte (human IgM 4.5 micrograms) and the monomer/reactant (acrylic acid-labeled 2H1, 5 micrograms) were incubated together, which resulted in the formation of a ternary complex or sandwich containing both monomer and reporter. Copolymerization of this complex with additional nonderivatized monomer (HEMA) resulted in the formation of fluorescent, polymer particles (sample a).

For comparison, a control sample was prepared that was identical to the first except the analyte was omitted. This resulted in the formation of polymer particles that contained monomer/reactant but not reporter/reactant, hence the polymer particles were non-fluorescent (sample b). To quantitatively compare the amounts of incorporation of fluorescence into the polymer particles from the two samples, they were subjected to quantitative flow analysis using a flow cytometer.

After the polymerization had proceeded for ten minutes, the suspension of polymer particles was diluted one-hundred-fold and then introduced into a flow cytometer (Becton Dickinson, FACS IV) equipped with an Argon ion laser light source. In this procedure, the suspended particles were carried single-file in a laminar stream of buffer. Interrogation of the particle stream with the laser beam generated light scatter each time a particle entered the laser pathway. The extent of the light scatter was a reflection of particle size and shape. The measurement of light scatter is used to electronically trigger a simultaneous measure of fluorescence emitted from the particle. In this way, fluorescence specifically associated with polymer particles can be selectively measured.

Figure 4:
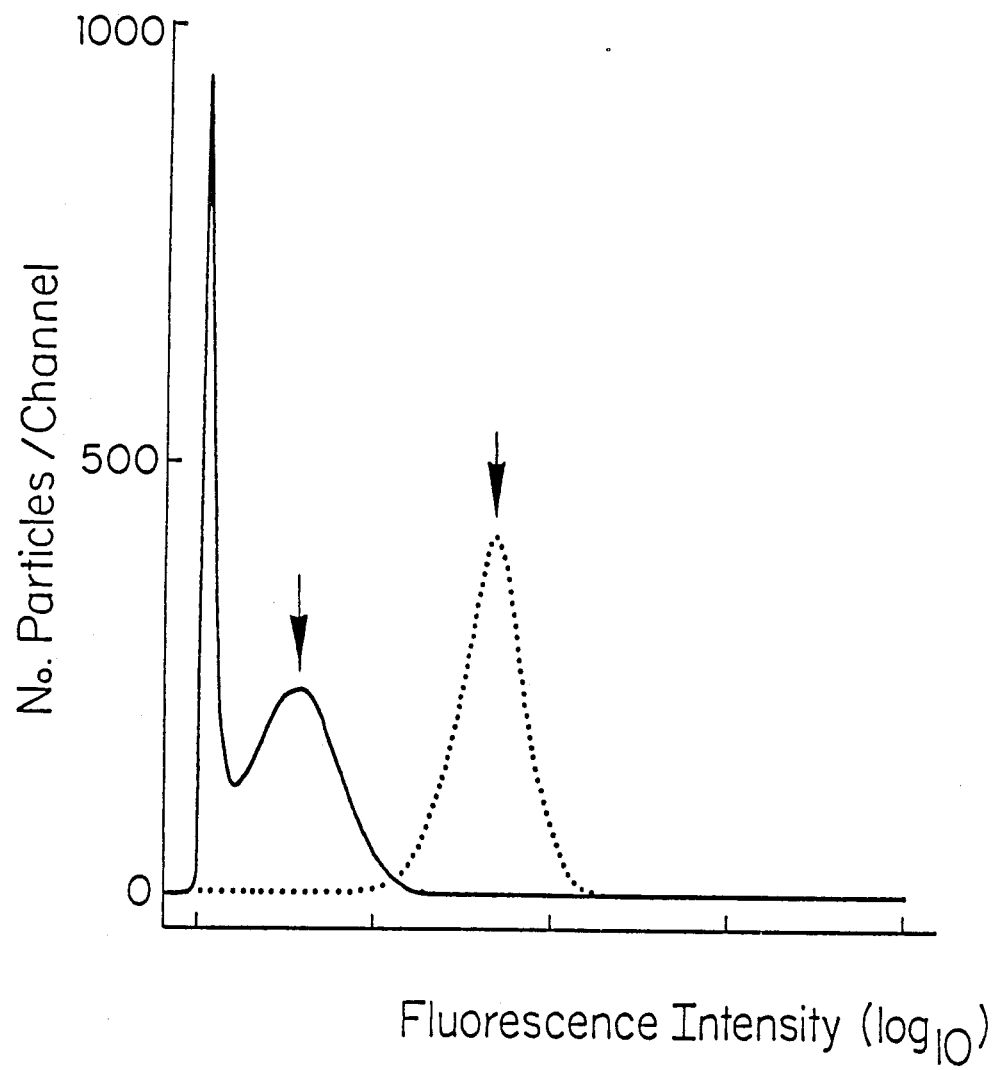
FIG. 4 depicts the incorporation of monomer/fluorescein tagged antibody reactant conjugates into reactant-containing polymer particles.
Figure 5:
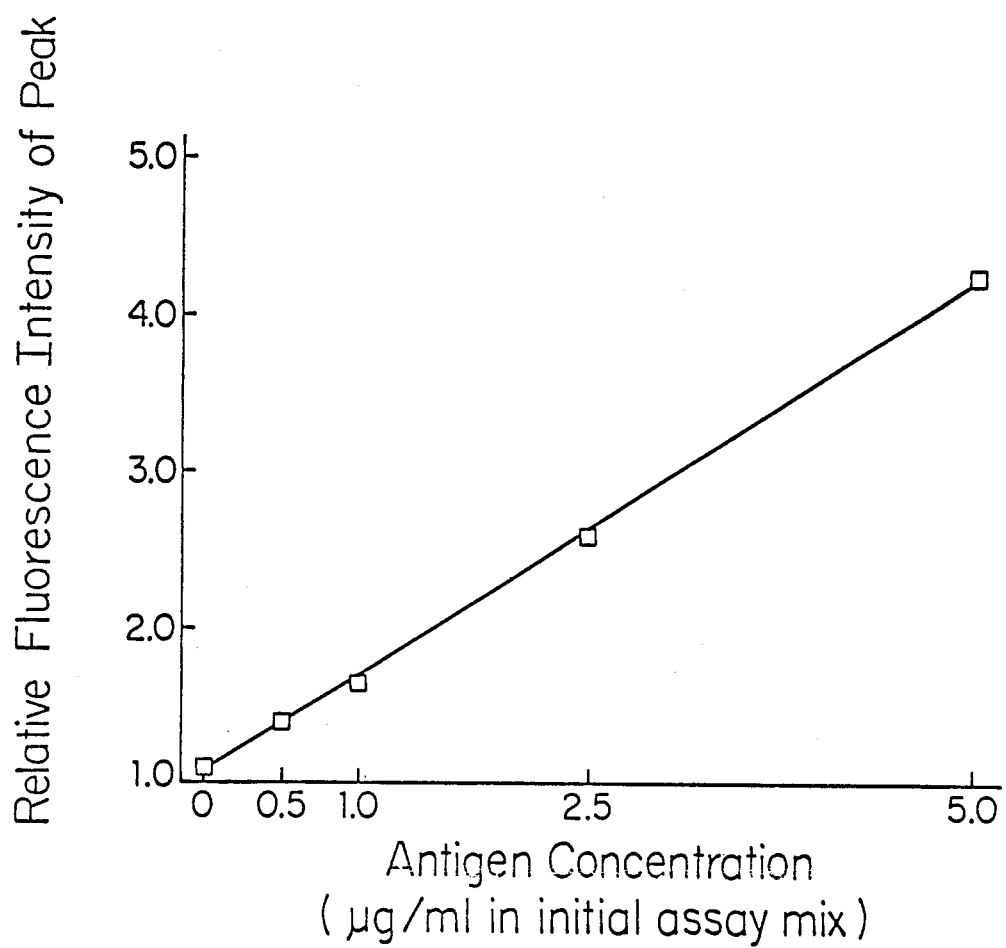
FIG. 5 is a diagram depicting the relationship between the fluorescence intensity and analyte concentration in one embodiment of the present invention.

The results are graphically presented in FIG. 4, which compares the fluorescence intensity of copolymer particles from a sample a (dotted line) with the fluorescence intensity of copolymer particles from a control sample b (solid line), from which the analyte was omitted. The fluorescence intensity of the copolymer particles formed in the presence of analyte (complete system) was shifted over 73 channels relative to the control (see arrows in FIG. 4). The fluorescence intensity scale (x axis) is logarithmic, and a shift of 73 channels corresponded to an 20-fold increase in fluorescence intensity. This increase in fluorescence intensity proved to be a linear function of the amount of analyte present in the sample. FIG. 5 is a plot of fluorescence intensity, on a linear scale, against the amount of analyte present in the sample, using 1 microgram of each reactant conjugate and otherwise the same conditions as used in FIG. 3.

Although the foregoing invention has been described in some detail by way of illustration and example for purposes of clarity of understanding, it will be obvious that certain changes and modifications may be practiced within the scope of the appended claims.

We claim:

1. An immunoassay method for determining the presence of an analyte in a fluid sample suspected of containing said analyte comprising:

(a) combining said fluid sample with a monomer/-reactant conjugate, capable of binding specifically to said analyte, in order to form a monomer/reactant conjugate—analyte complex, and a reporter/reactant conjugate, which binds specifically to said complex or to said analyte, for labeling said monomer/reactant conjugate—analyte complex, wherein said monomer is an addition polymerizable monomer;

(b) separating said labeled complex by initiating polymerization of the monomer/reactant conjugate—complex;

(c) detecting the incorporation of reporter into said polymerized complex as a measure of the analyte present in the sample.

2. The immunoassay method of claim 1 wherein said reporter/reactant conjugate is added after said complex formation.

3. An immunoassay method for determining the presence of an analyte in a fluid sample suspected of containing said analyte comprising:

(a) contacting said fluid sample with a monomer/analyte conjugate to form a fluid sample mixture, wherein said monomer is an addition polymerizable monomer;

(b) contacting said mixture with a reporter/reactant conjugate capable of specifically binding analyte to form reporter-labeled analyte complex and reporter-labeled monomer/analyte complex;

(c) separating said reporter-labeled monomer/analyte complex by initiating polymerization of the monomer/analyte-conjugate complex; and (d) detecting the incorporation of reporter into said polymerized complex as a measure of the analyte present in the sample.

4. The immunoassay method of claim 1 or 3 wherein the reporter is selected from the group consisting of radioisotopes, enzymes, enzyme inhibitors, enzyme cofactors, fluorophores, chemiluminescent materials, and chromophores.

5. The immunoassay method of claim 1 or 3, said monomer comprising a polymerizable, ethylenically unsaturated organic monomer selected from the group consisting of:

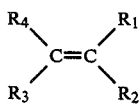

where $R_1$ is a hydrogen or lower alkyl having from 1 to 8 carbon atoms, $R_2$, is selected from the group consisting of

—H

—COCl

—COOH

—CO$_2$(CH$_2$)$_n$ OH (n = 1–8)

—CH$_2$NH$_2$

—CH$_2$Cl

—CO$_2$C$_2$H$_4$NHR (R = H or any organic group)

-continued

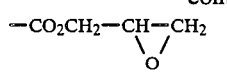

—CO$_2$CH$_2$CHOHCH$_2$OH

—CHO

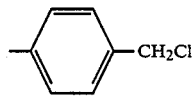

—CO$_2$(CH$_2$)$_n$NCO (n = 1–8)

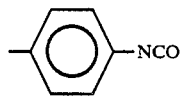

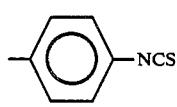

and $R_3$ and $R_4$ are selected from the group consisting of H and groups which will provide aliphatic unsaturation, with the proviso that one of $R_1$, $R_2$, $R_3$ or $R_4$ is other than H or lower alkyl.

6. The immunoassay method of claim 5 wherein $R_3$ and $R_4$ are H and $R_2$ is other than H.

7. The immunoassay method of claim 1 or 3 said monomer comprising an acetylenically unsaturated addition polymerizable monomer having a functional group capable of forming a covalent bond with an antibody, antigen or hapten.

8. The immunoassay method of claim 1 or 3 wherein the monomer is 2-hydroxyethyl methacrylate.

9. The immunoassay method of claim 1 or 3 wherein the reporter is fluorescein isothiocyanate.

10. The immunoassay method of claim 1 or 3 wherein the reactants and analytes are selected from the group consisting of antibodies, antigens and haptens.

11. The immunoassay method of claim 10 wherein the analyte is an immunoglobulin.

12. The immunoassay method of claim 11 wherein the immunoglobulin is IgM.

13. The immunoassay method of claim 12 wherein the IgM is human IgM.

14. The immunoassay method of claim 1 or 3 further comprising detecting the incorporation of reporter into the polymerized complex by flow cytometry.

15. A monomer/reactant conjugate for use in immunoassays, comprising:

an immunoglobulin covalently bonded to at least one addition polymerizable, ethylenically unsaturated organic monomer, wherein the organic monomer is selected from a group consisting of ethylenically unsaturated monomers having at least one reactive site for conjugating with the immunoglobulin.

16. The conjugate of claim 15 wherein the organic monomer is soluble in water or water/polar organic solvent mixtures.

17. The conjugate of claim 15, said monomer comprising a polymerizable, ethylenically unsaturated organic monomer selected from the group consisting of:

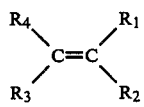

where $R_1$ is a hydrogen or lower alkyl having from 1 to 8 carbon atoms, $R_2$, is selected from the group consisting of

—H

—COCl

—COOH

—$CO_2(CH_2)_n$ OH (n = 1-8)

—$CH_2NH_2$

—$CH_2Cl$

—$CO_2C_2H_4NHR$ (R = H or any organic group)

—$CO_2CH_2$—CH—$CH_2$
\ /
O

—$CO_2CH_2CHOHCH_2OH$

—CHO

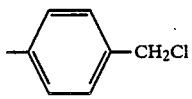

—$CO_2(CH_2)_n NCO$ (n = 1-8)

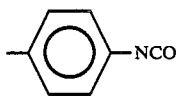

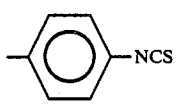

and $R_3$ and $R_4$ are selected from the group consisting of H and groups which will provide aliphatic unsaturation, with the proviso that one of $R_1$, $R_2$, $R_3$ or $R_4$ is other than H or lower alkyl.

18. The conjugate of claim 17 wherein $R_3$ and $R_4$ are H and $R_2$ is other than H.

19. The conjugate of claim 15 wherein the immunoglobulin is IgM.

20. The conjugate of claim 19 wherein the IgM is human Igm.

* * * * *